United States Patent [19]

Willis

[11] 4,346,997
[45] Aug. 31, 1982

[54] POSITIVE PRESSURE MAINTENANCE FOR SAMPLE PRESENTATION

[75] Inventor: Robert F. Willis, Greensboro, N.C.

[73] Assignee: Burlington Industries, Inc., Greensboro, N.C.

[21] Appl. No.: 157,841

[22] Filed: Jun. 9, 1980

[51] Int. Cl.³ .......................... G01N 21/57; G01J 3/46
[52] U.S. Cl. .................................... 356/244; 356/402; 356/445
[58] Field of Search ................ 356/244, 245, 238, 402, 356/445; 350/63

[56] References Cited

U.S. PATENT DOCUMENTS

| | | | |
|---|---|---|---|
| 2,022,327 | 11/1935 | Sheldon | 356/244 X |
| 2,701,980 | 2/1955 | Abbott | 356/244 X |
| 3,488,674 | 1/1970 | Simjian | 51/217 |
| 3,890,049 | 6/1975 | Collins et al. | 356/445 X |
| 3,976,288 | 8/1976 | Cuomo, Jr. | 269/21 |
| 4,037,830 | 7/1977 | Poluzzi et al. | 269/21 |

OTHER PUBLICATIONS

"New Reflectometer and its use for Whiteness Measurement", Hunter, JOSA, vol. 50, #1, Jan. 1960, pp. 44-48.

*Primary Examiner*—Vincent P. McGraw
*Attorney, Agent, or Firm*—Cushman, Darby & Cushman

[57] ABSTRACT

The invention relates to a method of presenting a non-rigid sample to a color measuring instrument, and such an instrument modified in accordance with the invention to provide proper sample presentation. Fluid under pressure is continuously supplied to the head of a conventional colorimeter having an open viewing port, to maintain a positive pressure in the head with respect to its immediate surroundings, fluid being exhausted through the open viewing port in a turbulent flow of about 10-20 cubic feet/minute. Then a solid backing structure is disposed in backing relationship with a non-rigid sample to be examined, and the sample is positioned over the viewing port with sufficient pressure applied to it to prevent the sample from moving away from the viewing port as a result of fluid flow through the viewing port. The fluid providing a positive pressure is exhausted from a location—a secondary opening about 1/10 the effective area of the viewing port—distinct from the viewing port when the viewing port is covered with the sample to be examined. The fluid flow through the instrument head prevents sample lint and dust from entering the head, facilitates removal of heat generated by the instrument, and facilitates maintenance of the sample so that a flat, distortion-free surface can be examined.

25 Claims, 6 Drawing Figures

POSITIVE PRESSURE MAINTENANCE FOR SAMPLE PRESENTATION

BACKGROUND AND SUMMARY OF THE INVENTION

In the utilization of color measuring instruments, particularly reflectance instruments, having a head with an open viewing port, it is highly desirable to present samples to the instrument so that a flat distortion-free surface can be measured without compromising the repeatability and accuracy of the instrument. This goal can prove elusive when non-rigid samples (e.g. fabric samples) are being presented.

Prior art techniques for presenting non-rigid samples to a color measuring instrument are of two basic types. In the first method, the instrument viewing port is covered with an optical glass cover which protects the instrument optics from dust and lint, and allow the instrument to view a flat sample surface (essentially for repeatable results). In the second prior art method, the instrument viewing port is left open and the sample placed directly over the open port. While the color measuring instrument can be utilized according to such prior art techniques, both of these prior methods have drawbacks associated therewith.

When the first prior art method described above is utilized, there is increased heat buildup in the instrument (primarily from the light source within the instrument), and occasional distortion of the sample surface and inconsistent results due to changes in the glass cover caused by scratches, smudges, dust, and moisture. A commonly practiced solution to this problem is to utilize a heat sink to radiate excess temperature from the instrument. This heat sink is effective only at relatively low ambient air temperatures, below about 85° F., and requires that the instrument be unconfined, i.e., not mounted within a desk. For speed, convenience, and safety it has become desirable for these instruments often to be mounted within a desk, thereby decreasing the effectiveness of the heat sink. Problems encountered in utilizing the second prior art method described above are the tendency of the non-rigid (e.g. fabric) samples to "bow" or "balloon" into the open viewing port, presenting a surface which is not flat, and the buildup of dust and lint (especially from fabric samples) within the instrument, adversely affecting the accuracy thereof.

According to the present invention a method and apparatus are provided that overcome most of the problems associated with prior art utilization techniques for color measuring instruments. According to the present invention it is possible to present non-rigid samples to a color measuring instrument so that a flat, distortion-free surface can be measured without compromising the repeatability and accuracy of the instrument. The invention is practiced, in its most basic terms, by providing a positive pressure of fluid (e.g. filtered air) within the instrument head, provision being provided for maintenance—but no undue buildup—of the positive pressure even when the viewing port is covered with a sample to be examined.

According to one aspect of the present invention, a method of presenting a non-rigid sample to a color measuring instrument having a head with an open viewing port is provided which comprises the following steps: Continuously supplying fluid under pressure to the instrument head to exhaust through the viewing port to prevent sample lint and dust from entering the head, to facilitate removal of heat generated by the instrument, and to facilitate maintenance of a sample so that a flat, distortion-free surface can be examined; and exhausting the fluid supply from the instrument head from a location distinct from the viewing port when the viewing port is covered with a sample to be examined. Preferably, the method comprises the further steps of disposing a backing structure in backing relationship with a non-rigid sample to be examined, and positioning the backed non-rigid sample over the viewing port with sufficient pressure to prevent the sample from moving away from the viewing port as a result of a fluid flow toward the viewing port. The fluid supplying step is preferably practiced by supplying a turbulent flow of filtered gas at a flow rate of about 10–20 cubic feet per minute through the viewing port with no sample in place, and the exhausting step is preferably practiced by providing a secondary opening having about 1/10 the effective area of the viewing port and spaced from the viewing port.

According to another aspect of the present invention there is provided a method of presenting a non-rigid sample to a color measuring instrument having a head with an open viewing port, consisting essentially of practicing the following steps substantially sequentially: Continuously supplying fluid under pressure to the instrument head to maintain the positive pressure in the head with respect to its immediate surroundings, fluid being exhausted through the open viewing port. Disposing a backing structure in backing relationship with a non-rigid sample to be examined. Positioning the backed non-rigid sample over the viewing port with sufficient pressure to prevent the sample from moving away from the viewing port as a result of fluid flowing through the viewing port; and exhausting the fluid providing a positive pressure in the instrument head from a location distinct from the viewing port when the viewing port is covered with the sample to be examined.

According to a further aspect of the present invention there is provided a method of modifying an existing color measuring instrument having a head with an open viewing port. According to this aspect of the invention a secondary opening is provided in the head having an effective area through which fluid can flow substantially smaller than the effective area of the viewing port through which fluid can flow. Then, a source of pressurized fluid is operatively connected to the head to provide fluid to the head to exhaust through the viewing port, or when the viewing port is covered, through the secondary opening, to prevent sample lint and dust from entering the head, to facilitate removal of heat generated by the instrument, and to facilitate maintenance of a sample so that a flat, distortion-free surface can be examined.

Apparatus according to the present invention comprises an instrument having a head with means defining an open port in the head over which a sample is adapted to be placed, and a source generating unwanted head located in the head (e.g. a lamp). The instrument further comprises means defining a secondary opening in the head spaced from and distinct from the port, the secondary opening being substantially smaller in effective cross-sectional area than the port; and means for providing fluid under pressure to the head and operatively connected to the head to exhaust fluid through the port, and when the port is covered, through the secondary opening. Pressure-applying means are disposed adjacent the port on the head for positioning a backed sample in place over the port without allowing movement thereof away from the port as a result of fluid flow through the port. The effective cross-sectional area of the secondary opening is about 1/10 that of the port, and the means for providing fluid under pressure is capable of delivering filtered gas under pressure to the head so that a turbulent flow of gas exhausts through the port when it is open, at a flow rate of about 10-20 cubic feet per minute.

Apparatus according to the present invention further comprises a color measuring instrument having a head with an open viewing port, and means for presenting a non-rigid sample to the instrument. The presenting means comprises means for continuously supplying fluid under pressure to the instrument head to exhaust through the viewing port to prevent sample lint and dust from entering the head, to facilitate removal of heat generated by the instrument, and to facilitate maintenance of a sample so that a flat, distortion-free surface can be examined; and means for providing exhausting of the fluid supplied to the instrument head from a location distinct from the viewing port when the viewing port is covered with a sample to be examined.

It is the primary object of the present invention to provide a simple, effective method and apparatus for presenting non-rigid samples to an instrument, particularly a color measuring instrument, so that a flat, distortion-free surface can be measured without compromising the repeatability and accuracy of the instrument. This and other objects of the invention will become clear from an inspection of the detailed description of the invention, and from the appended claims.

DETAILED DESCRIPTION OF THE DRAWINGS

Figure 4:
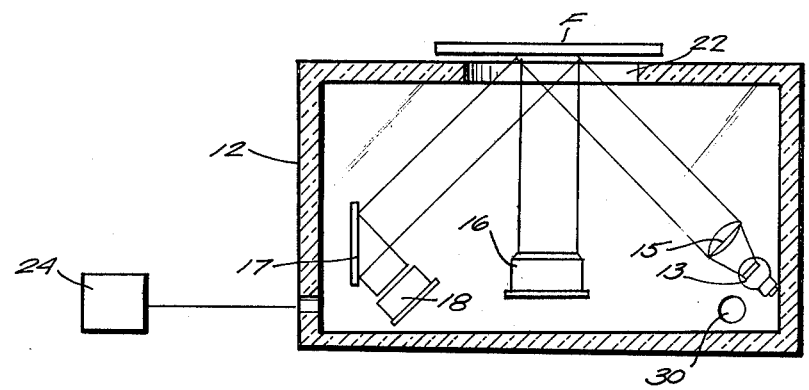
FIG. 4 is a schematic, cross-sectional view of the internal workings of an exemplary color measuring instrument for practicing the method according to the present invention.
Figure 5:
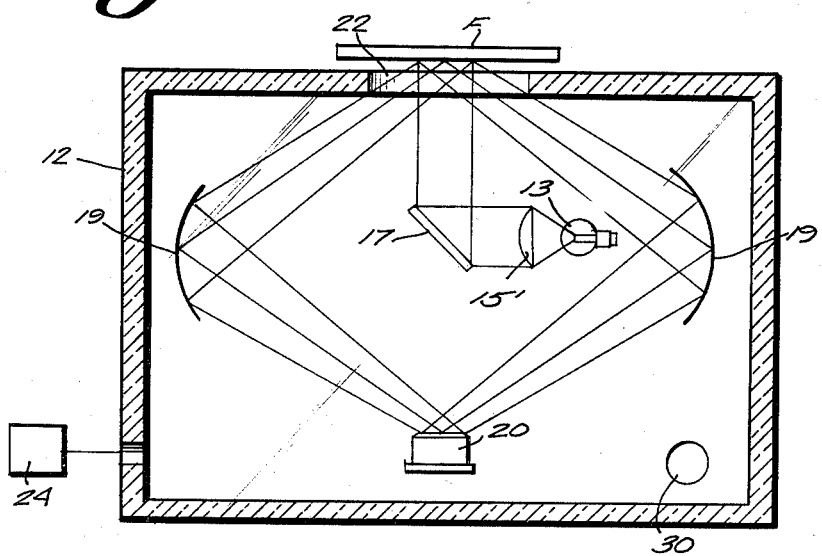
FIG. 5 is a view like that of FIG. 4 showing modified form of color measuring instrument with which the method according to the invention may be practiced.

A conventional color measuring instrument for practicing the method according to the present invention, and modified to provide the apparatus according to the present invention, is shown generally at 10 in the drawings. The color measuring instrument, which may be a Hunter D-25 Colorimeter, or like color measuring instrument (particularly reflectance instruments) comprises a head 12, and includes an internal light source (e.g. lamp) 13, and various other internal structures for effecting color measurement. Conventional interior components that may be utilized in the instrument 10 are illustrated schematically in FIGS. 4 and 5. For instance in FIG. 4 the structure 10 includes a lens 15, test cell 16, mirror 17, and comparison cell 18. In the conventional structure of FIG. 5 a lens 15', mirror 18, ellipsoid or annular mirrors 19, and photocell 20 are provided.

The head 12 of the color measuring instrument 10 has an open viewing port 22 provided therein. In use of the device 10, there often is a tendency for lint and dust to pass through the opening 22 into the internal workings of the device 10, non-rigid samples may bow or balloon into the opening 22, and when the opening 22 is covered by an optical glass cover there tend to be undesirable variations in color measurement due to smudges and scratches on the glass, and also undesirable heat buildup in the device 10. According to the present invention all of such drawbacks are substantially overcome.

Figure 1:
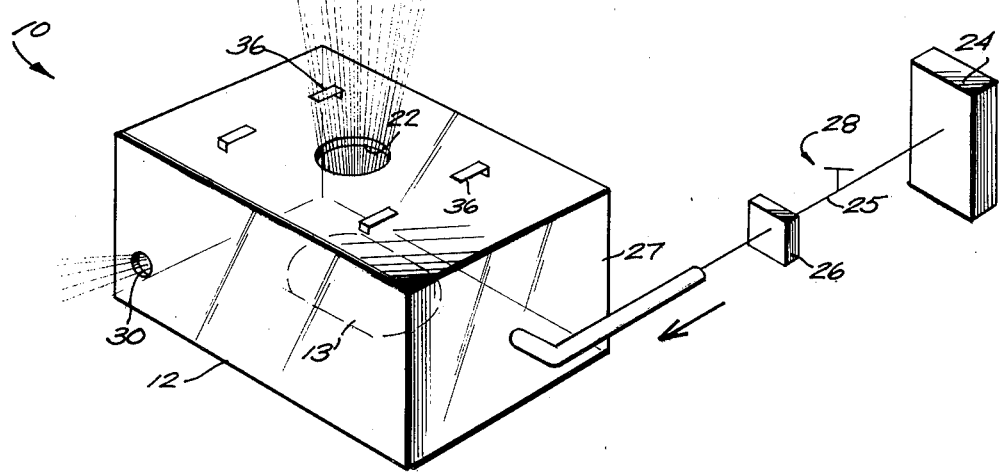
FIG. 1 is a schematic perspective view of an exemplary color measuring instrument according to the present invention in a non-use mode.
Figure 2:
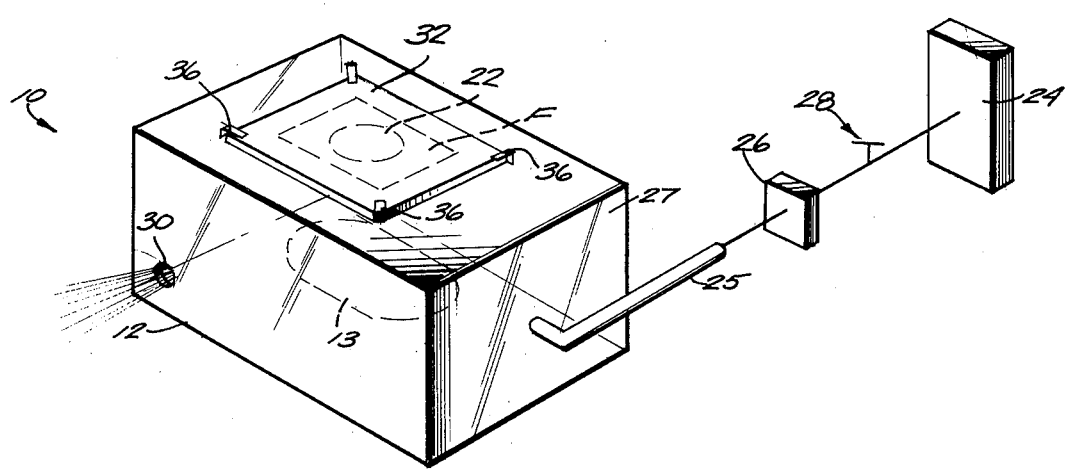
FIG. 2 is a view similar to FIG. 1 showing a non-rigid sample disposed over the viewing port of the invention.

According to the present invention, the color measuring instrument 10 comprises means for presenting a non-rigid sample to the instrument, the presenting means comprising means for continuously supplying fluid under pressure to the instrument head 12 to exhaust through the viewing port 22 to prevent sample lint and dust from entering the head, to facilitate removal of heat generated by the instrument (e.g. lamp 13) and to facilitate maintenance of a sample so that a flat, distortion-free surface can be examined; and means for providing exhausting of the fluid supplied to the instrument head 12 from a location distinct from the viewing port 22 when the viewing port 22 is covered with a sample to be examined (see FIG. 2). The means for continuously supplying fluid under pressure preferably comprises a conventional source 24 of air under pressure, which passes through conduit 25 through a filter 26 through a wall 27 of the head 12. A valve 28, or like structure, can be provided to meter the flow through the conduit 25 to adjust the flow rate. The source 24 (as metered by the valve 28) is capable of supplying a turbulent flow of filtered gas under pressure to the head 12 so that gas exhausting through the viewing port (see FIG. 1) has a flow rate of about 10-20 cubic feet per minute when the viewing port is uncovered. At this flow rate, the flow is great enough to protect the instrument from lint and prevent bowing or ballooning of the non-rigid sample into the viewing port 22, but small enough so that undue difficulties in mounting the sample are not encountered.

Figure 6:
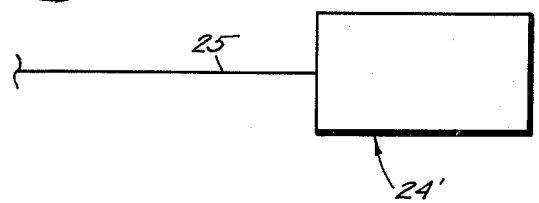
FIG. 6 is a schematic detail view of a modified form of air pressure source that may be utilized according to the invention.

In the modification illustrated in FIG. 6, the source of air under pressure, 24', is a fan with a built-in filter.

The means for providing exhausting of fluid supplied to the instrument 12 according to the present invention comprises means defining a secondary opening 30 in a convenient portion of the head 12. Preferably the opening 30 is constructed so that it has an effective cross-sectional area through which fluid can flow of substantially less—preferably 1/10—the effective cross-sectional area of the open viewing port 22. Airflow through secondary opening 30 facilitates removal of heat generated by the instrument even during sample viewing, while continuing to allow a positive pressure to be maintained within the head 12.

Figure 3:
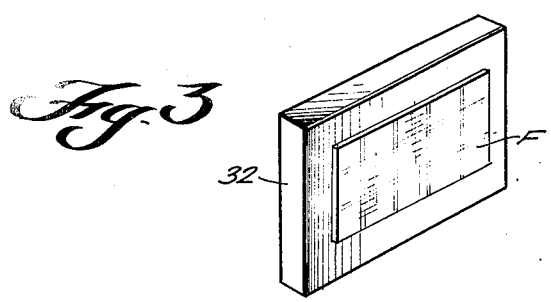
FIG. 3 is a perspective view of an exemplary non-rigid sample and backing structure adapted for presentation to the instrument of FIGS. 1 and 2.

A typical non-rigid sample, such as a fabric sample, to be presented to the color measuring instrument 10 according to the present invention is illustrated at F in the drawings. Preferably, a solid backing structure is provided for the non-rigid sample F. One form that the backing structure may take is the rigid plate 32 illustrated in FIG. 3. The plate 32 is shown as transparent in the drawings; however, depending upon the type of instrument 10 with which it is utilized it may be opaque if desired.

If desired, means may be provided for facilitating holding of the sample F to the backing structure, although that is not absolutely necessary. It is desirable, however, to provide means associated with the head 12 for applying pressure to the backed sample F to hold it in place over the viewing port 22 without allowing movement thereof away from the port 22 as a result of fluid flow through the port. Such pressure applying means may take the form of a plurality of clamps 36 surrounding and adjacent to the viewing port 22, which are adapted to move into engagement with the backing plate 32 to hold it in place, with the non-rigid sample F directly over the viewing port 22 (see FIG. 2).

According to one aspect of the method of the present invention, an existing color measuring instrument 10 having a head 12 with an open viewing port 22 is modified. This modification is effected by: Providing a secondary opening 30 is the head 12 having an effective area through which fluid can flow substantially smaller than the effective area of the viewing port 22 through which fluid can flow (e.g. 1/10 the effective area); and, operatively connecting a source 24 of pressurized fluid (e.g. air that is filtered) to the head 12 (e.g. through conduit 25) to provide fluid to the head 12 to exhaust through the viewing port 22, or when the viewing port 22 is covered by the sample F, through the secondary opening 30, to prevent sample lint and dust from entering the head, to facilitate removal of heat generated by the instrument (e.g. lamp 13), and to facilitate maintenance of the sample F so that a flat, distortion-free surface can be examined.

A method of presenting a non-rigid sample F to the color measuring instrument 10 modified according to the above-described method consists essentially of the steps of substantially sequentially: (a) Continuously supplying fluid under pressure to the instrument head 12 to maintain a positive pressure in the head with respect to its immediate surroundings, fluid being exhausted through the open viewing port 22. (b) Disposing a backing structure (e.g. plate 32) in backing relationship with a non-rigid sample F to be examined. (c) Positioning the backed non-rigid sample F over the viewing port 22 with sufficient pressure (e.g. utilizing clamps 36) to prevent the sample F from moving away from the viewing port 22 as a result of fluid flow through the viewing port. And (d) exhausting the fluid providing a positive pressure in the instrument head 12 from a location distinct from the viewing port (secondary opening 30) when the viewing port is covered with the sample to be examined (see FIG. 2). Step (a) is practiced by supplying a turbulent flow of filtered air at a flow rate of about 10–20 cubic feet per minute through the viewing port 22 with no sample F in place (see FIG. 1). Step (d) is preferably practiced by providing a secondary opening 30 in the instrument head 12 spaced from the viewing port 22 and having an effective area through which fluid can flow of about 1/10 the effective area of the viewing port through which fluid can flow.

It will thus be seen that according to the present invention a method and apparatus have been provided for presenting non-rigid samples to a color measuring instrument so that a flat, distortion-free surface can be measured without compromising the repeatability and accuracy of the instrument. By providing the particular airflow according to the present invention, lint and dust are prevented from entering the head 12, heat generated by the lamp 13 or other components is removed to keep the temperature of the instrument within acceptable levels, and the maintenance of a non-rigid sample F so that it does not bow or balloon into the viewing port 22, but provides a flat, distortion-free surface that can be examined, is facilitated.

While the invention has been herein shown and described in what is presently conceived to be the most practical and preferred embodiment thereof, it will be apparent to those of ordinary skill in the art that many modifications may be made thereof within the scope of the invention, which scope is to be accorded to the broadest interpretation of the appended claims so as to encompass all equivalent methods and apparatus.

What is claimed is:

1. A method of presenting a non-rigid sample to a color measuring instrument having a head with an open viewing port, comprising the steps of
    (a) continuously supplying fluid under pressure to the instrument head to exhaust through the viewing port to prevent sample lint and dust from entering the head, to facilitate removal of heat generated by the instrument, and to facilitate maintenance of a sample so that a flat, distortion-free surface can be examined; and
    (b) exhausting the fluid supplied to the instrument head from a location distinct from the viewing port when the viewing port is covered with a sample to be examined.

2. A method as recited in claim 1 comprising the further steps of (c) disposing a solid backing structure in backing relationship with a non-rigid sample to be examined; and (d) positioning the backed non-rigid sample over the viewing port with sufficient pressure to prevent the sample from moving away from the viewing port as a result of fluid flow toward the viewing port.

3. A method as recited in claim 1 wherein step (a) is practiced by supplying a turbulent flow of filtered gas at a flow rate of about 10–20 cubic feet/min. through the viewing port with no sample in place.

4. A method as recited in claims 1, 2 or 3 wherein step (b) is practiced by providing an opening in the instrument head having an effective area through which fluid can flow substantially smaller than the area of the viewing port through which fluid can flow.

5. A method as recited in claim 2 wherein step (a) is practiced by supplying a turbulent flow of gas at a flow rate of about 10–20 cubic feet/min. through the viewing port with no sample in place.

6. A method of presenting a non-rigid sample to a color measuring instrument having a head with an open viewing port consisting essentially of the steps of substantially sequentially
    (a) continuously supplying fluid under pressure to the instrument head to maintain a positive pressure in the head with respect to its immediate surroundings, fluid being exhausted through the open viewing port;
    (b) disposing a solid backing structure in backing relationship with a non-rigid sample to be examined;
    (c) positioning the backed non-rigid sample over the viewing port with sufficient pressure to prevent the sample from moving away from the viewing port as a result of fluid flow through the viewing port; and (d) exhausting the fluid providing a positive pressure in the instrument head from a location distinct from the viewing port when the viewing port is covered with the sample to be examined.

7. A method as recited in claim 6 wherein step (a) is practiced by supplying a turbulent flow of filtered gas at a flow rate of about 10–20 cubic feet/min. through the viewing port with no sample in place.

8. A method as recited in claims 6 or 7 wherein step (d) is practiced by providing an opening in the instrument head spaced from the viewing port and having an effective area through which fluid can flow of about 1/10 the effective area of the viewing port through which fluid can flow.

9. A method of modifying an existing color measuring instrument having a head with an open viewing port, comprising the steps of
(a) providing a secondary opening in the head having an effective area through which fluid can flow substantially smaller than the effective area of the viewing port through which fluid can flow; and
(b) operatively connecting a source of pressurized fluid to the head to provide fluid to the head to exhaust through the viewing port, or when the viewing port is covered through the secondary opening, to prevent sample lint and dust from entering the head, to facilitate removal of heat generated by the instrument, and to facilitate maintenance of a sample so that a flat, distortion-free surface can be examined.

10. A method as recited in claim 9 wherein step (b) is practiced by operatively connecting a source of gas to the instrument head capable of supplying a turbulent flow of filtered gas at a flow rate of about 10–20 cubic feet/min. through the viewing port with no sample in place.

11. A method as recited in claim 10 wherein step (a) is practiced by forming the secondary opening so that it is about 1/10 the effective area of the viewing port.

12. A method as recited in claim 9 wherein step (a) is practiced by forming the secondary opening so that it is about 1/10 the effective area of the viewing port.

13. A method as recited in claims 9, 10, 11, or 12 comprising the further step of providing pressure-applying means adjacent the viewing port on the instrument head for positioning a backed, non-rigid sample in place over the viewing port without allowing movement thereof away from the viewing port as a result of fluid flow through the viewing port.

14. An instrument having a head with means defining an open port in said head over which port a sample is adapted to be placed, and a source generating unwanted heat in said head, said instrument further comprising:
means defining a secondary opening in said head spaced from and distinct from said port, said secondary opening being substantially smaller in effective cross-sectional area than said port; and
means for providing fluid under pressure to said head and operatively connected to said head to exhaust fluid through said port, and when said port is covered through said secondary opening.

15. An instrument as recited in claim 14 further comprising pressure-applying means adjacent said port and on said head for positioning a backed sample in place over said port without allowing movement thereof away from said port as a result of fluid flow through said port.

16. An instrument as recited in claim 14 wherein said means defining said secondary opening defines said secondary opening so that its effective cross-sectional area is about 1/10 that of said port.

17. An instrument as recited in claim 14 wherein said means for providing fluid under pressure is capable of delivering filtered gas under pressure to said head so that a turbulent flow of gas exhausting through said port when it is open has a flow rate of about 10–20 cubic feet/min.

18. An instrument as recited in claims 14, 15, 16, or 17 wherein said instrument is a color measuring instrument for measuring the color of non-rigid samples, and wherein said port is an open viewing port.

19. A color measuring instrument having a head with an open viewing port, and means for presenting a non-rigid sample to said instrument, said presenting means comprising
means for continuously supplying fluid under pressure to said instrument head to exhaust through the viewing port to prevent sample lint and dust from entering the head, to facilitate removal of heat generated by the instrument, and to facilitate maintenance of a sample so that a flat, distortion-free surface can be examined; and
means for providing exhausting of the fluid supplied to said instrument head from a location distinct from said viewing port when said viewing port is covered with a sample to be examined.

20. A color measuring instrument as recited in claim 19 further comprising pressure-applying means adjacent said viewing port on said head for positioning a backed sample in place over said port without allowing movement thereof away from said port as a result of fluid flow through said port.

21. A color measuring instrument as recited in claim 19 wherein said means for providing exhausting of fluid from a location distinct from said viewing port have an effective cross-sectional area through which fluid can flow of about 1/10 the effective cross-sectional area of said open viewing port.

22. A color measuring instrument as recited in claims 19, 20 or 21 wherein said means for continuously supplying pressurized fluid to said instrument head comprises means capable of supplying a turbulent flow of filtered gas under pressure to said instrument head so that gas exhausting through said viewing port has a flow rate of about 10–20 cubic feet/min. when said viewing port is uncovered.

23. A method as recited in claims 1, 5, 9 or 11 wherein steps (a) and (b) are practiced so that a positive pressure with respect to its immediate surroundings is always maintained in the head.

24. An instrument as recited in claim 14 wherein said means defining a secondary opening and said means for providing fluid under pressure comprise means for maintaining a positive pressure in said head with respect to its immediate surroundings.

25. An instrument as recited in claim 19 wherein said means for continuously supplying fluid under pressure and said means for providing exhausting of the fluid comprise means for maintaining a positive pressure in said head with respect to its immediate surroundings.

* * * * *